United States Patent [19]

Weiss et al.

[11] Patent Number: 4,918,104

[45] Date of Patent: Apr. 17, 1990

[54] METHOD AND COMPOSITION FOR INCREASING THE CONCENTRATION OF OMEGA-3 POLYUNSATURATED FATTY ACIDS IN POULTRY AND POULTRY EGGS AND POULTRY AND EGGS RESULTING THEREFROM

[76] Inventors: Howard S. Weiss, 45 Hillpark Ave., Great Neck, N.Y. 11021; Carl S. Schwartz, R.D. 2192 Kirby La., Muttontown, N.Y. 11791

[21] Appl. No.: 62,890

[22] Filed: Jun. 16, 1987

[51] Int. Cl.$^4$ ............................................. A61K 31/20
[52] U.S. Cl. ....................................... 514/560; 800/2; 800/DIG. 5
[58] Field of Search .......................................... 514/560

[56] References Cited

U.S. PATENT DOCUMENTS 2,879,162  3/1959  Baldini et al. ...................... 514/560

FOREIGN PATENT DOCUMENTS 216658  9/1986  Japan ................................... 514/560

OTHER PUBLICATIONS

Derwent Abstract of J6 0169-418A, 2/15/84.
Derwent Abstract of J5 7086-254, 11/18/80.
Derwent Abstract of J6 2163-669A.
Derwent Abstract of J6 0132-916A.

*Primary Examiner*—Frederick E. Waddell
*Attorney, Agent, or Firm*—John P. White

[57] ABSTRACT

This invention provides a method of increasing the concentration of omega-3, polyunsaturated fatty acids in poultry which comprises administering to the poultry an effective amount of preformed omega-3, polyunsaturated fatty acid or a metabolic precursor thereof.

The invention also involves a poultry feed composition useful in effecting this result.

Also disclosed is a method of increasing the concentration of omega-3, polyunsaturated fatty acids in poultry eggs which comprises administering to the poultry egg layers an effective amount of preformed omega-3, polyunsaturated fatty acid or a metabolic precursor thereof.

Further disclosed is a chicken and a poultry egg, each having omega-3, polyunsaturated fatty acids at a concentration greater than that which naturally occurs or is normally present.

7 Claims, 2 Drawing Sheets

EPA AND DHA IN POULTRY BREAST, LEG AND FAT EXPRESSED AS PERCENT OF TOTAL LIPIDS

METHOD AND COMPOSITION FOR INCREASING THE CONCENTRATION OF OMEGA-3 POLYUNSATURATED FATTY ACIDS IN POULTRY AND POULTRY EGGS AND POULTRY AND EGGS RESULTING THEREFROM

BACKGROUND OF THE INVENTION

Throughout this application, various publications are referenced by arabic numbers within parentheses. Full citations for these publications may be found at the end of the specification, immediately preceding the claims. The disclosures of these publications in their entireties are hereby incorporated by references into this application in order to describe more fully the state of the art to which this invention pertains.

Fish-eating communities (as in Denmark and Japan) have a markedly decreased incidence of coronary artery disease. Eskimo communities like-wise have a reduced incidence of coronary artery disease despite their heavy consumption of whale blubber (See generally, Refs. 1, 2, 3, 4, 5, 6 and 7). The mechanism of this reduced incidence of heart disease may only be secondarily correlated with a low serum cholesterol, but more importantly with a measurable tendency for decreased platelet adhesiveness (8, 9) and decreased whole blood viscosity (10). This, in turn, may be explained by the replacement in part, of arachidonic acid by omega-3 (n-3) polyunsaturated fatty acids (PUFA) in the cell membranes and the resultant changes in the functional properties of the prostaglandins derived from these.

It is theorized that dietary omega-3 polyunsaturated fatty acids such as eicosapentaenoic acid (EPA) and docosahexaenoic acid (DHA) may provide one of the best means of primary prevention of coronary artery disease through their effects on plasma lipids and platelet function. Of equal importance is the possible secondary prevention of progressive coronary artery atherosclerosis and peripheral vascular disease through similar mechanisms (i.e., cholesterol concentration, blood viscosity and platelet aggregability) (See, generally, Refs. 8-27) Omega-3 polyunsaturated fatty acids also may have a role in the treatment of specific illnesses (i.e. lupus, hypertension and immune problems) (See, e.g., Refs. 27, 28, 29, 30, 31, 32 and 33).

At this time, existing sources of dietary omega-3 PUFA are completely limited to fish and other marine animals (e.g., seals, whales), rare plants, and commercial extracts of whole fish as a liquid or encapsulated oil. (See, e.g., Refs. 34–41) Most land animals and vegetables have extremely low concentrations of eicosapentaenoic acid and docosahexaenoic acid. Furthermore, fish and other marine animals seem to be acceptable and easily available only to coastal fishing communities with a long history of fish as food. Most of the industrial land-locked communities find fish to be both too expensive and less appealing taste wise when compared to land animal meats. In addition, commercially available, highly refined fish oils are very expensive (refining of fish oil is necessary to limit potential toxic components such as vitamins A and D) (42). As daily dietary supplements, these fish oils lack taste appeal and are plagued by problems of user compliance.

In response to the above-mentioned shortcomings, this invention creates an alternative food which can provide a significant source of omega-3 PUFA without necessitating the consumption of fish or fish oils.

The experiments set forth herein establish a method of increasing the concentration of omega-3 PUFA in poultry and eggs for the purpose of creating a class of poultry and eggs with concentrations of omega-3 PUFA greater than that naturally occurring. The method involves administering to poultry an effective amount of either preformed omega-3 PUFA or a metabolic precursor thereof.

SUMMARY OF THE INVENTION

This invention provides a method of increasing the concentration of omega-3, polyunsaturated fatty acids in poultry. The method comprises administering to the poultry an effective amount of preformed omega-3, polyunsaturated fatty acid or a metabolic precursor thereof.

Also disclosed is a poultry feed which comprises an amount of preformed omega-3, polyunsaturated fatty acid or a metabolic precursor thereof effective to increase the concentration of omega-3, polyunsaturated fatty acid in poultry which eat the feed.

The invention further discloses a chicken which comprises omega-3, polyunsaturated fatty acids at a concentration greater than that which naturally occurs or is normally present in poultry.

Additionally, this invention provides a method of increasing the concentration of omega-3, polyunsaturated fatty acids in poultry eggs. The method comprises administering to the poultry egg layers an effective amount of preformed omega-3, polyunsaturated fatty acid or a metabolic precursor thereof.

Finally, this invention discloses a poultry egg which comprises omega-3, polyunsaturated fatty acids at a concentration greater than that which normally occurs or is normally present in poultry eggs.

BRIEF DESCRIPTION OF THE FIGURES

FIG. 1 is a graphic representation of data from Table 1 and identifies feed compositions F-213, F-214, F-215 and F-216. Linolenic acid (Lin) values are not reflected in this figure. Omega-3 content values are only expressed for EPA and DHA. EPA and DHA are plotted additively, so that the combined percentage of these two substances can be observed.

FIG. 2 reflects the omega-3 profile of the entire edible portion of breast and leg, both raw and cooked.

DETAILED DESCRIPTION OF THE INVENTION

Figure 1:
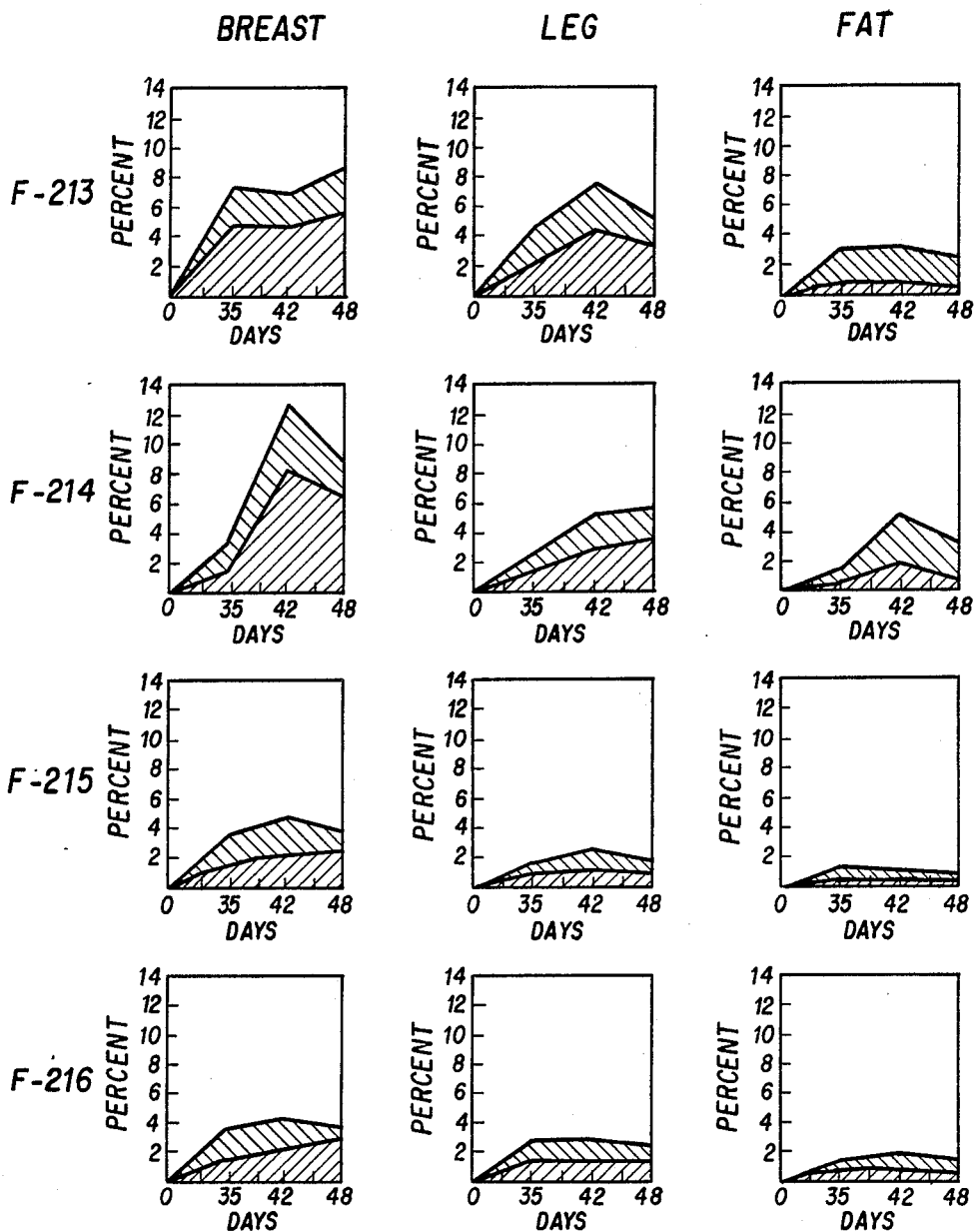
FIG. 1. EPA and DHA in Poultry Breast, Leg and Fat, Expressed as Percent of Total Lipids.

This invention provides a method of increasing the concentration of omega-3, polyunsaturated fatty acids in poultry. The method comprises administering to the poultry an effective amount of preformed omega-3, polunsaturated fatty acid or a metabolic precursor thereof.

Further disclosed is a poultry feed which comprises an amount of preformed omega-3, polyunsaturated fatty acid or a metabolic precursor thereof effective to increase the concentration of omega-3, polyunsaturated fatty acid in poultry which eat the feed.

Examples of the metabolic precursors which may be employed in this invention include linolenic acid, linseed oil, fish or a fish derivative, algae, and an omega-3 polyunsaturated fatty acid having a carbon chain of less than about 18 carbons.

This invention also discloses a chicken which comprises omega-3, polyunsaturated fatty acids at a concentration greater than that which naturally occurs or is normally present in poultry.

Additionally, this invention provides a method of increasing the concentration of omega-3, polyunsaturated fatty acids in poultry eggs. The method comprises administering to the poultry egg layers an effective amount of preformed omega-3, polyunsaturated fatty acid or a metabolic precursor thereof. The presently preferred metabolic precursor is menhaden oil and the presently preferred amount of menhaden oil comprises at least 5% by weight of the poultry's diet.

Finally, this invention discloses a poultry egg, which comprises omega-3, polyunsaturated fatty acids at a concentration greater than that which normally occurs or is normally present in poultry eggs.

Experimental Details

First Series of Experiments

METHOD

Step 1 - Experimental Feeding Trials

Several experimental feeding trials were tested as part of the omega-3 polyunsaturated fatty acid project design. Each trial was identified by a letter/number code. The trials varied with respect to the number of birds and pens employed, the type of feed treatments utilized, and the timing of the particular feeding programs.

Trial FR-26-86

The objective of this trial was to determine the EPA/DHA profile of carcass fat produced by various dietary regimes. The trial involved experimental feed treatments F-126 through F-129. (See Table 1). The feeding program was as follows:

0-21 Days=Common Starter (mixed-FR-24-86)
22-42 Days=Experimental Finisher
43-48 Days=Experimental Withdrawal Four pens, with 100 birds per pen, were employed in this trial. The density of each pen was 0.80 sq. ft. per bird. All birds were banded according to their pen and diet. Body weights and feed conversions were collected at 21, 42 and 48 days of age. The birds were pulled from the processing line after being eviscerated, chilled, and then carried to the carcass lab.

TABLE 1

Feed Compositions: The following feed composition trials were used in this invention

| TMT | | |
|---|---|---|
| TRIAL #: FR-32-86 | | |
| F-164 | Control (6% Poultry Meal) | |
| F-126 | Corn | 60.66% |
| | Soybean Meal | 18.02% |
| | Gluten Meal | 7.66% |
| | Poultry Meal | 6.00% |
| | Meat-Bone Meal | 4.00% |
| | Poultry Fat | 2.08% |
| | Limestone | 0.56% |
| | Salt | 0.43% |
| | Premix | 0.59% |
| F-165 | Experimental (6% Poultry Meal + 2% Linseed Oil) | |
| F-127 | Corn | 60.66% |
| | Soybean Meal | 18.02% |
| | Gluten Meal | 7.66% |
| | Poultry Meal | 6.00% |
| | Meat-Bone Meal | 4.00% |

TABLE 1-continued

Feed Compositions: The following feed composition trials were used in this invention

| TMT | | |
|---|---|---|
| | Linsesd Oil | 2.08% |
| | Limestone | 0.56% |
| | Salt | 0.43% |
| | Premix | 0.59% |
| F-166 | Experimental (10% Fish Meal) | |
| F-128 | Corn | 64.06% |
| | Soybean Meal | 13.98% |
| | Fish Meal | 10.00% |
| | Gluten Meal | 8.54% |
| | Poultry Fat | 1.94% |
| | Limestone | 0.54% |
| | Salt | 0.42% |
| | Premix | 0.52% |
| F-167 | Experimental (7% Fish Meal + 1% Linseed Oil) | |
| F-129 | Corn | 63.18% |
| | Soybean Meal | 13.86% |
| | Gluten Meal | 10.56% |
| | Fish Meal | 7.00% |
| | Meat-Bone Meal | 2.18% |
| | Linseed Oil | 1.00% |
| | Poultry Fat | 0.76% |
| | Limestone | 0.54% |
| | Salt | 0.42% |
| | Premix | 0.50% |
| TRIAL #: FR-41-86 | | |
| F-213 | Experimental (10% Menhaden Oil) | |
| F-214 | Corn | 46.42% |
| | Soybean Meal | 22.81% |
| | Menhaden Oil | 10.00% |
| | Gluten Meal | 8.60% |
| | Animal Blend | 6.00% |
| | Brewex | 2.00% |
| | Blood Meal | 1.60% |
| | CDP | 0.90% |
| | Limestone | 0.68% |
| | Salt | 0.31% |
| | Premix | 0.68% |
| F-215 | Experimental (10% Linseed Oil) | |
| F-216 | Corn | 46.42% |
| | Soybean Meal | 22.81% |
| | Linseed Oil | 10.00% |
| | Gluten Meal | 8.60% |
| | Animal Blend | 6.00% |
| | Brewex | 2.00% |
| | Blood Meal | 1.60% |
| | CDP | 0.90% |
| | Limestone | 0.68% |
| | Salt | 0.31% |
| | Premix | 0.68% |

Individual color scores were performed on all birds. Thereafter, the birds were frozen in storage facilities.

Trial FR-32-86

This project was designed to determine whether increasing dietary levels of fish meal or sources rich in linolenic acid (e.g., linseed oil) would produce broilers that contained high levels of omega-3, polyunsaturated fatty acids. The working hypothesis was that broilers consuming diets containing fish meal and/or linseed oil would contain higher levels of omega-3, polyunsaturated fatty acids than broilers fed the control diet containing 6% poultry meal and poultry fat.

The birds were fed experimental feed treatments F-164 through F-167 (see Table 1). The feeding program was set up as follows:

0-21 Days=Common Starter (mixed for FR-27-86)
22-48 Days=Experimental Finisher

Eight pens, with 90 male birds per pen, were employed in this trial. The density of each pen was 0.80 square feet per bird. Body weights and feed conversions at 21, 42 and 48 days of age. One hundred birds per treatment were collected, banded and then recovered from the processing line after eviscerating. The birds were iced down and transported to the carcass lab for individual color scores. After scoring, the birds were frozen and stored for taste panel work.

Taste panelists evaluated breast and thigh meat from FR-32-86 using the Hedonic Preference Evaluation. All four treatments were included. First the panelists evaluated the breast meat as a group of then they tasted the dark meat. The meat was baked in the lab and warmed up in the microwave prior to serving. Overall (white and dark meat), there was a significant difference between F-165 and F-167, F-165 and F-166, F-164 and F-167, and F-164 and F-166. Looking at white meat only, there was no significant difference. However, with the dark meat, there was a significant difference between all the treatments. The panelists were influenced by whether or not the chicken meat was white or dark. Below is the data:

HEDONIC PREFERENCE EVALUATION
Smiley Score

|  | F-164 | F-165 | F-166 | F-167 |
|---|---|---|---|---|
| White Meat | | | | |
| Average | 3.29 | 3.31 | 3.43 | 3.34 |
| Std. Dev. | 1.43 | 1.43 | 1.42 | 1.37 |
| Dark Meat | | | | |
| Average | 3.54 | 4.11 | 2.16 | 2.66 |
| Std. Dev. | 1.20 | 1.41 | 1.16 | 1.43 |

Preference:
White Meat: F-164 - 33%  Dark Meat: F-165 - 55%
F-166 - 31%  F-164 - 25%
F-165 - 22%  F-167 - 14%
F-167 - 14%  F-166 - 3%
 none - 3%

General Comments:
(White Meat)

| | |
|---|---|
| F-164 | Taste - bland; good; aftertaste |
| | Tenderness - tender |
| | Moistness - dry slightly dry very dry |
| | Texture - smooth; chewy |
| F-165 | Taste - bland; good; okay |
| | Tenderness - split between tough and tender |
| | Moistness - dry slightly dry very dry |
| | Texture - chewy; stringy; smooth; good |
| F-166 | Taste - good; fishy; not tasty/funny |
| | Tenderness - split between slightly tough and tender |
| | Moistness - dry slightly dry moist very dry |
| | Texture - smooth; chewy |
| F-167 | Taste - bland; good; unfamiliar |
| | Tenderness - very tender tender |
| | Moistness - dry very dry slightly dry |
| | Texture - good; smooth; stringy |

(Dark Meat)

| | |
|---|---|
| F-164 | Taste - bland; okay; good |
| | Tenderness - tender very tender |
| | Moistness - moist; split between very moist, dry, and slightly dry |
| | Texture - smooth; stringy; greasy; good |
| F-165 | Taste - good; bland; okay |
| | Tenderness - tender very tender |
| | Moistness - moist; split between dry and very moist |
| | Texture - smooth; good; soggy; greasy |
| F-166 | Taste - awful, fishy; strange |
| | Tenderness - tender |
| | Moistness - split between dry and moist |
| | Texture - smooth; greasy; stringy; good |
| F-167 | Taste - awful; bland; fishy; strange; old |
| | Tenderness - tender |
| | Moistness - moist; split between slightly moist and dry |

HEDONIC PREFERENCE EVALUATION
Smiley Score

Texture - smooth; chewy; good

One breast half was cubed for the taste panel and the other half was sheared for tenderness. Overall, the breasts were tender. Below is the data:

| | Tenderness (kgs./gms.) | | | |
|---|---|---|---|---|
| | F-164 | F-165 | F-166 | F-167 |
| Average | 4.31 | 3.48 | 4.97 | 3.76 |
| Std. Dev. | 1.41 | 0.58 | 1.68 | 1.30 |
| No. 6.00 | 1 | 0 | 4 | 1 |
| Range | 3.01– 7.65 | 2.22– 4.27 | 3.05– 7.17 | 1.89– 6.45 |
| No. Birds | 10 | 10 | 11 | 11 |

Trial FR-45-86

This trial was designed to evaluate the effect on tissue omega-3 levels and the taste acceptance for broilers fed menhaden and linseed oils at several inclusion levels over various production time periods. Experimental feed treatments F-235 through F-252 (see Table 2) were used in this trial. The feeding program was as follows.

0-21 Days = Experimental Starter
22-43 Days = Experimental and/or Common Finisher
44-48 Days = Experimental or Common Withdrawal Seventy-two pens, with 100 birds per pen, were employed. The density of each pen was 0.80 square feet per bird. Body weights and feed conversions were collected at 21, 43 and 48 days of age. On treatments F-236, F-239, F-242, F-245, F-248 and F-251, feeders were weighed and dumped only at 35 days. Two birds per pen (1 male and 1 female) were collected, the wings banded, and then each was processed at 3, 4, 5 and 6 weeks of age. This resulted in 4 males and 4 females per dietary treatment at each of the above ages. Of this group, one male and one female per treatment were shipped fresh on excess dry ice for fatty acid profiles. The remaining birds were frozen and stored for future analysis. At 48 days of age, 40 birds per treatment (20 males and 20 females) were banded and processed; of this group one male and one female per treatment were collected and shipped on excess dry ice for fatty acid profiles. The remaining 38 birds per treatment were used in taste panel evaluation. The balance of all treatments were processed and scored for color and finish at 49 days of age.

TABLE 2
Trial FR-45-86
EXPERIMENTAL TREATMENTS:

| Source | Level | Experimental Feed Period | Common Feed Period |
|---|---|---|---|
| F-235 | Menhaden Oil | 2½% | Day 1–Day 48 | — |
| F-236 | Menhaden Oil | 2½% | Day 1–Day 36 | Day 37–Day 48 |
| F-237 | Menhaden Oil | 2½% | Day 1–Day 21 | Day 22–Day 48 |
| F-238 | Menhaden Oil | 5% | Day 1–Day 48 | — |
| F-239 | Menhaden Oil | 5% | Day 1–Day 36 | Day 37–Day 48 |
| F-240 | Menhaden Oil | 5% | Day 1–Day 21 | Day 22–Day 48 |
| F-241 | Menhaden Oil | 10% | Day 1–Day 48 | — |
| F-242 | Menhaden Oil | 10% | Day 1–Day 36 | Day 37–Day 48 |
| F-243 | Menhaden Oil | 10% | Day 1–Day 21 | Day 22–Day 48 |
| F-244 | Linseed Oil | 2½% | Day 1–Day 48 | — |
| F-245 | Linseed Oil | 2½% | Day 1–Day 36 | Day 37–Day 48 |
| F-246 | Linseed Oil | 2½% | Day 1–Day 21 | Day 22–Day 48 |

TABLE 2-continued
Trial FR-45-86
EXPERIMENTAL TREATMENTS:

| | Source | Level | Experimental Feed Period | Common Feed Period |
|---|---|---|---|---|
| F-247 | Linseed Oil | 5% | Day 1–Day 48 | — |
| F-248 | Linseed Oil | 5% | Day 1–Day 36 | Day 37–Day 48 |
| F-249 | Linseed Oil | 5% | Day 1–Day 21 | Day 22–Day 48 |
| F-250 | Linseed Oil | 10% | Day 1–Day 48 | — |
| F-251 | Linseed Oil | 10% | Day 1–Day 36 | Day 37–Day 48 |
| F-252 | Linseed Oil | 10% | Day 1–Day 21 | Day 22–Day 48 |

| | | | | | |
|---|---|---|---|---|---|
| F-214 | 24–27 Days | 28–34 Days | 28–42 Days Menhaden Oil 35–42 Days | 42–48 Days | |
| F-215 | 24–27 Days | | Linseed Oil 28–42 Days | 42–48 Days | |
| F-216 | 24–27 Days | 28–34 Days | Linseed Oil 35–42 Days | 42–48 Days | |

Feeding Program:
24–27 Days = Common Finisher
28–42 Days OR 35–42 Days (See Above) = Experimental Grower
42–48 Days = Common Withdrawal I

FR-45-86
WEST

| | | | | | |
|---|---|---|---|---|---|
| F-235 | 9, 16, 42, 51 | F-249 | 71 | SECTION #4 | F-236 | 72 |
| F-236 | 25, 34, 59, 72 | F-240 | 69 | | F-245 | 70 |
| F-237 | 6, 29, 47, 58 | F-239 | 67 | | F-247 | 68 |
| F-238 | 10, 11, 46, 55 | F-247 | 65 | | F-244 | 66 |
| F-239 | 1, 4, 50, 67 | F-245 | 63 | | F-249 | 64 |
| F-240 | 24, 35, 48, 69 | F-244 | 61 | | F-252 | 62 |
| F-241 | 12, 15, 45, 52 | F-236 | 59 | | F-246 | 60 |
| F-242 | 20, 27, 37, 54 | F-248 | 57 | | F-237 | 58 |
| F-243 | 7, 18, 44, 49 | F-238 | 55 | | F-250 | 56 |
| | | F-246 | 53 | SECTION #3 | F-242 | 54 |
| | | F-235 | 51 | | F-241 | 52 |
| | | F-243 | 49 | | F-239 | 50 |
| | | F-237 | 47 | | F-240 | 48 |
| | | F-241 | 45 | | F-238 | 46 |
| | | F-252 | 43 | | F-243 | 44 |
| | | F-250 | 41 | | F-235 | 42 |
| | | F-251 | 39 | | F-248 | 40 |
| | | F-242 | 37 | | F-251 | 38 |

Pen Size = 8' × 10' (80 sq. ft.)

FEED ROOM

| | | | | | |
|---|---|---|---|---|---|
| F-244 | 22, 31, 61, 66 | F-240 | 35 | SECTION #2 | F-245 | 36 |
| F-245 | 23, 36, 63, 70 | F-249 | 33 | | F-236 | 34 |
| F-246 | 2, 3, 53, 60 | F-244 | 31 | | F-249 | 32 |
| F-247 | 14, 17, 65, 68 | F-237 | 29 | | F-251 | 30 |
| F-248 | 8, 21, 40, 57 | F-242 | 27 | | F-250 | 28 |
| F-249 | 32, 33, 64, 71 | F-236 | 25 | | F-252 | 26 |
| F-250 | 5, 28, 41, 56 | F-245 | 23 | | F-240 | 24 |
| F-251 | 13, 30, 38, 39 | F-248 | 21 | | F-244 | 22 |
| F-252 | 19, 26, 43, 62 | F-252 | 19 | | F-242 | 20 |
| | | F-247 | 17 | SECTION #1 | F-243 | 18 |
| | | F-241 | 15 | | F-235 | 16 |
| | | F-251 | 13 | | F-247 | 14 |
| | | F-238 | 11 | | F-241 | 12 |
| | | F-235 | 9 | | F-238 | 10 |
| | | F-243 | 7 | | F-248 | 8 |
| | | F-250 | 5 | | F-237 | 6 |
| | | F-246 | 3 | | F-239 | 4 |
| | | F-239 | 1 | | F-246 | 2 |

EAST

Feeding Trial FR-41-86

This trial was designed to determine whether feeding extremely high levels of menhaden oil (10%) or linseed oil for one or two weeks during the grower phase would elevate tissue levels of omega-3 fatty acids in broilers processed at seven seeks of age. Consumer acceptance was evaluated in a taste panel study to determine whether such high levels of menhaden oil or linseed oil caused objectionable flavors in the final products.

The feed treatments employed in this trial were F-213 through F-216. (see Table 1) The experimental feed treatments and feeding program were as follows:

Experimental Treatments:

| | Common Finisher | Common Grower | Common Grower | Experimental Withdrawal I | Common |
|---|---|---|---|---|---|
| F-213 | 24–27 | | | Menhaden Oil | 42–48 Days |

Four pens, with 60 male birds per pen, were employed in this trial. The density of each pen was 0.80 square feet per pen. Two whole, processed male birds per treatment were collected at 28, 35, 42 and 48 days of age. Samples then were shipped with excess dry ice for fatty acid profiles. No bird or feed weighing was necessary. Feeders were dumped at all feed changes. The remaining birds were processed by treatment and frozen for later panel evaluation.

Step #2 Sample Preparation

Chemical preparation of tissue samples remained constant throughout the project. The term "chemical" refers to the extraction of crude lipids from the tissue sample and conversion to methyl esters (transesterification).

The following is a description delineating the evolution of sample handling.

Precision dissection

Whole birds were delivered to the laboratory under dry ice. The birds then were defrosted and grouped as per feed treatment. Using a scalpel, a core sample was removed from the breast (white meat), thigh (dark meat), fat, and skin. The term "core" is used to describe a sample derived by precision dissection, free of contamination by other tissue types (i.e. breast tissue devoid of fat or skin). The quantity of tissue sample started out at 100 gm for each of the four types. After establishing the representative concentration of crude lipids found in each tissue type, the sample size was adjusted to yield one gram of crude lipid after extraction. The resultant sample size was as follows:
1. Breast=50 gm
2. Leg =25 gm
3. Fat=1 gm
4. Skin analysis is was discontinued when it became obvious that it duplicated the information gathered from fat.

Real World Dissection

The term "Real World" refers to an attempt to duplicate a typical portion which would be eaten by the consumer. The following is a description of each "Real World" type:

"REAL WORLD BREAST" was comprised of all edible tissue referred to as breast by the consumer. This included muscle, skin, and fat.

"REAL WORLD LEG" contained all edible tissue found in the thigh and leg, including muscle, skin, and fat.

Depot Fat Dissection

After reviewing the initial data, the decision was made to focus efforts on increasing omega-3 PUFA concentration in fat (including leaf fat), hereinafter called depot fat. The other tissue types (core, breast and leg) being more metabolically active, are closer to blood levels of omega-3 PUFA, give consistently higher values, but realistically contribute less to real world sample levels of omega-3 PUFA than depot fat. The harvesting of depot fat is hereinafter referred to as depot fat dissection.

Current Dissection Technique

"Depot Fat Dissection" was employed at the ages of 21, 28, 35 and 42 days. At 49 days, when the animal is normally prepared for consumer use, whole birds were received and tested using "Real World Dissection".

Step #3 Analysis of Long Chain Fatty Acids in Foods and Blood : Brief Summary

The sample was homogenized with chloroform:methanol 2:1 to quantitatively extract the total crude lipids. The fatty acids from triacylglycerides, phosphatides and cholesterol esters were converted into methyl esters by a transesterification reaction using sodium methoxide. The resulting methyl esters were then analyzed by capillary gas chromatography and mass spectrophotometry (Perkin-Elmer/Finnigan Mass Spectrophotometer-Ion Trap).

Step #4: Extraction:

Methanol was added to the weighed sample in step #1, in a homogenizing vessel of appropriate size, and in a volume representing 10X the sample weight (10 ml methanol/gram of sample). The sample was homogenized for one minute, taking care to avoid excessive heat generation. Added next was a volume of chloroform which was 2X the amount of methanol added previously (20 ml chloroform/gram of sample). The sample was homogenized once again for 2 minutes.

Then, the sample was centrifuged and the supernatant was filtered into a suction flask through Whattman #1 filter paper in a buchner funnel. Celite analytical filtering aid was used, if necessary, to promote faster flow.

The filtrates were then transfered quantitatively into a separatory funnel of appropriate volume. A small portion of chloroform:methanol 2:1 was used to rinse the suction flask and to insure quantitative transfer of extract into the separatory funnel.

A volume of 0.88% potassium chloride in water, equal to 25% the volume of organic extract, was next added to the separatory funnel. The mixture was shaken vigorously, then allowed to settle. When the phase separation was complete (both layers were clear and no emulsion existed at the interface), the bottom organic layer was drained off into a second clean separatory funnel of the same size and was washed with a mixture of water:methanol 1:1, the volume of which was equal to 25% that of the organic layer. After complete phase separation, the bottom organic layer, which contained the purified lipids, again was drained off into an erlenmeyer flask of appropriate volume and fitted with a ground glass stopper. Two grams of anhydrous sodium sulfate were added and the flask was shaken to dry the extract. The flask was then swirled to rinse the sodium sulfate down to the bottom and the solution was decanted into a round bottom flask of appropriate volume, with care taken to leave the sodium sulfate behind.

Step #5 Concentration and Isolation :

A round bottom flask was connected to a rotary evaporator using a trap and the solvent was removed at or near room temperature and under reduced pressure. (temperature may be up to 40 degrees centigrade). The solvent was not evaporated to dryness, but rather concentrated to a small volume (about 25 ml). The extract was quantitatively transferred from the round bottom flask into a tared 25×150 mm test tube, using a small portion of chloroform:methanol 2:1 to rinse the flask. The tube was placed in a heating block calibrated to 40 degrees centigrade and the extract was evaporated to dryness using a gentle stream of nitrogen. The tube was weighed, subtracting the tare weight, and the weight of total crude lipid present was calculated. This value then was recorded for future reference.

Immediately after weighing the extract, the lipid was redissolved in petroleum ether to a concentration of 30 mg/ml. The headspace was flushed with nitrogen and the tube stoppered.

At the end of this step, a solution of crude lipid extract in petroleum ether was prepared in a volumetric flask, at a concentration at or near 25 mg/ml. The concentration then was recorded. Then, 1.0 ml of this solution was transferred into a 15 ml teflon lined screwcapped vial and 1.0 ml of methanoic base reagent was added, mixed and stoppered tightly.

Step #6 Transesterification :

The vial was heated at 80 degrees centigrade for 20 minutes in a heating block and allowed to cool to room temperature. Following this, 3 ml of water and 3 ml of diethylether were added to the vial and mixed well. After complete phase separation had occurred, the lower aqueous layer was removed, using a pasteur pipet, and discarded. The organic layer (petroleum ether/diethylether/fatty acid methyl ester solution) was washed once more with 3 ml of water. Once again, the aqueous layer was discarded and removed. A small amount of anhydrous sodium sulfate then was added to the test tube. The tube was shaken to dry the contents over sodium sulfate and the contents then were transferred quantitatively into a 5 ml reaction vial using a pasteur pipet. The volume was adjusted to exactly 4.0 ml either by exaporation with nitrogen or by adding petroleum ether. The vial was stoppered tightly with a mininert valve and stored in the freezer until ready for gas chromatograph analysis.

Step #7 Gas Chromatographic Analysis:

From the vial prepared in step #4, 0.1 microliters were withdrawn and injected into a Perkin-Elmer Sigma 2000 Gas Chromatograph equipped with a microprocessor to control four level temperature programming, flame ionization detector and capillary injector for split/splitness operation and using the following conditions:

Injection Temperature 250 degrees centrigrade
Split Mode Ration 100:1
Column Temperature Program 150 to 220 at 2 degrees centigrade/minute
Attenuation 4 to 16 FID
Detector Temperature 250 degrees centigrade
Carrier Flow Rate 0.7–1.0 ml/minute helium The resulting chromatogram was observed and the parameters adjusted for optimum sensitivity and resolution. When necessary, the sample was diluted or concentrated.

Discussion

Table 3 represents eicosapentaenoic acid, docosahexanenoic acid and linolenic acid values in poultry breast, leg and fat. These values are expressed as a percentage of total lipids.

The areas in Table 3 which are crossbatched were designed to be experimental controls; however, chromatographic analysis indicates that these control animals have been fed feed containing significant amounts of linolenic acid; resulting i the expected abnormal quantities of EPA and DHA (metabilic conversion).

Table 3 illustrates the following:

Ba, La, & FA = Breat, Leg, and Fat at 35 days. (precision disection)

Bb, Lb, & Fb = Breast, Leg, and Fat at 42 days. (precision disection)

Bc, Lc, & Fc = Breast,m Leg, and Fat at 48 days. (precision disection).

Brwr & Lrwr = Breast, Leg, and Fat at 48 days. (real world raw disection)

Brwc & Lrwc = Breast, Leg, and Fat at 48 days. (real world cooked disection)

As is shown in FIG. 1, sample feed compositions F-213 and F-214 demonstrated an ability to generate 2% EPA in all three tissue types. DHA varied from 0.7% to over 6%, with the greatest values found in breast tissue. Furthermore, omega-3 increased rapidly with this feeding technique. FIG. 1 also shows that sample feed compositions F-215 and F-216 demonstrated a significant ability to generate metabolically EPA and DHA using the metabolic precursor linolenic acid in the feed.

Figure 2:
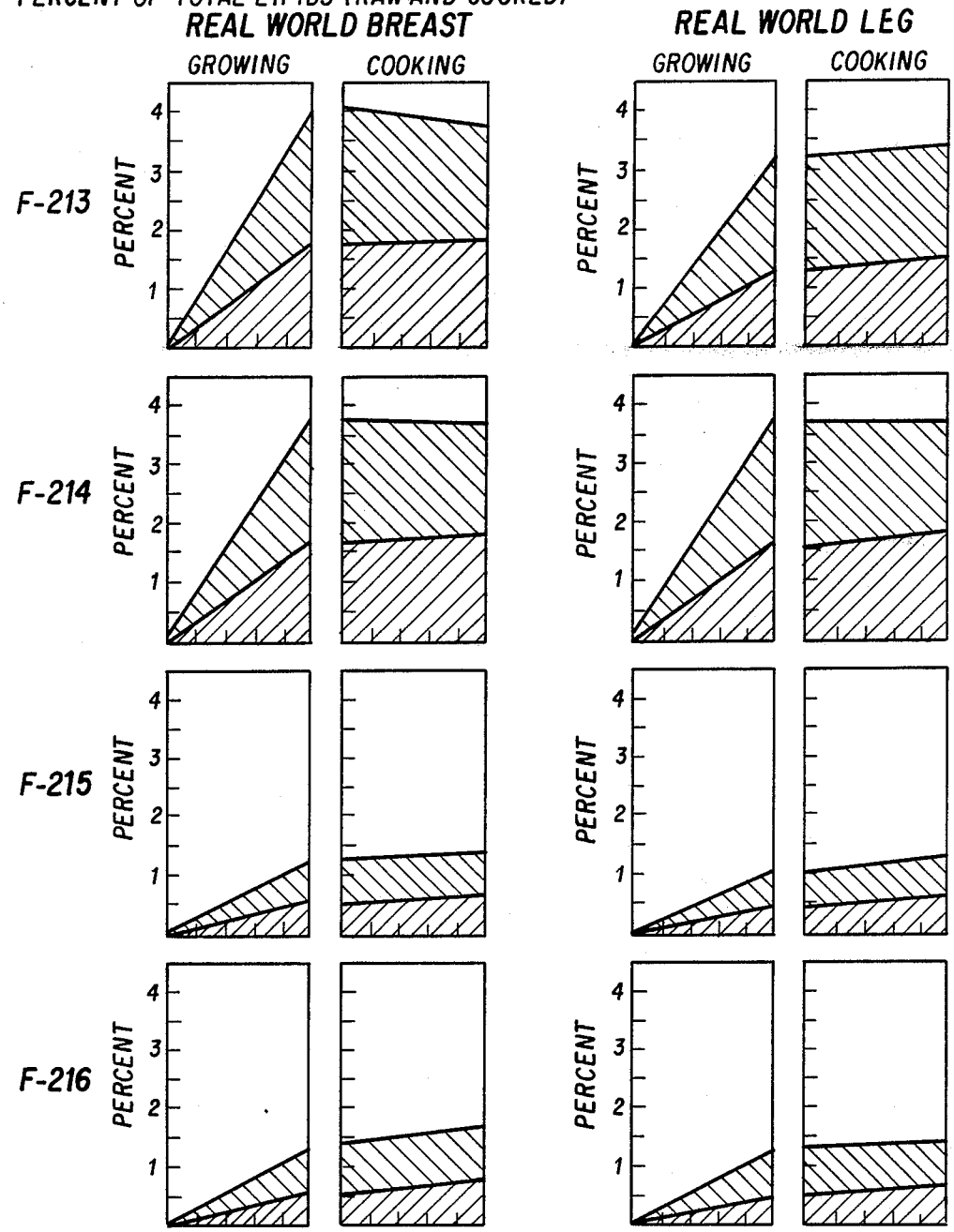
FIG. 2. EPA and DHA in Real World Poultry Breast and Leg, Expressed as Percent of Total Lipids.

As is evidenced in FIG. 2, "Real world" samples demonstrated the importance of elevating omega-3 levels in depot and subcutaneous fat. "Precision" tissue type disection revealed a lipid content of Breast = 1%, Leg = 2%; while "real world" disection yielded a lipid content of Breast = 7 ½% and Leg = 15%.

FIG. 2 illustrates the heat stability of EPA and DHA. Cooking tests conducted with fish have yielded similar results.

Second Series of Experiments

Method

Each egg was separated grossly into yolk and white. The white then was discarded. The egg yolk was analyzed using the same analysis employed and previously described in the first series of experiments.

Discussion

The "MARKET EGG" data charted in Table 4 resulted from an experiment designed to establish the level of naturally occurring n-3 PUFA found in eggs available to consumers.

The "Omega Egg" data charted on Table 5 reflects the n-3, PUFA levels obtained in eggs from hens fed on an experimental diet containing preformed and/or a metabolic precursor of n-3 PUFA. The source of the latter in this experiment was menhaden oil at a concentration of 5% by weight of the feed. Eggs were tested at weeks 1 thru 10. Organoleptic scoring of a taste panel indicated excellent taste and appeal.

TABLE 3

Quantitative Values for LIN, EPA and DHA Long Chain Fatty Acids In Poultry Breast, Leg and Fat

| | | Ba | La | Fa | Bb | Lb | Fb | Bc | Lc | Fc | Brwr | Lrwr | Brwc | Lrwc |
|---|---|---|---|---|---|---|---|---|---|---|---|---|---|---|
| 213 | LIN | 0.77 | 1.02 | 1.00 | 0.74 | 0.94 | 1.18 | 0.60 | 0.68 | 0.91 | 0.94 | 0.97 | 0.96 | 0.97 |
| 213 | EPA | 3.43 | 2.40 | 2.14 | 2.52 | 3.32 | 2.46 | 2.58 | 1.79 | 1.88 | 2.32 | 1.88 | 1.95 | 1.90 |
| 213 | DHA | 4.33 | 2.23 | 0.90 | 4.37 | 4.40 | 1.09 | 5.89 | 3.38 | 0.67 | 1.69 | 1.21 | 1.79 | 1.47 |
| | | Ba | La | Fa | Bb | Lb | Fb | Bc | Lc | Fc | Brwr | Lrwr | Brwc | Lrwc |
| 214 | LIN | 2.91 | 4.54 | 5.19 | 0.79 | 1.05 | 1.13 | 0.90 | 0.85 | 1.11 | 1.03 | 1.04 | 0.84 | 1.01 |
| 214 | EPA | 1.73 | 1.19 | 0.92 | 4.44 | 2.41 | 3.57 | 2.18 | 2.10 | 2.49 | 2.07 | 2.17 | 1.87 | 1.91 |
| 214 | DHA | 1.84 | 1.45 | 0.58 | 8.11 | 2.76 | 1.96 | 6.62 | 3.67 | 1.02 | 1.60 | 1.56 | 1.75 | 1.27 |
| | | Ba | La | Fa | Bb | Lb | Fb | Bc | Lc | Fc | Brwr | Lrwr | Brwc | Lrwc |
| 215 | LIN | 7.74 | 11.74 | 13.09 | 8.21 | 13.49 | 14.80 | 7.13 | 10.55 | 12.16 | 10.98 | 11.85 | 8.66 | 9.60 |
| 215 | EPA | 1.78 | 0.86 | 0.68 | 2.53 | 1.41 | 0.75 | 1.86 | 0.92 | 0.66 | 0.71 | 0.64 | 0.79 | 0.65 |
| 215 | DHA | 1.77 | 0.80 | 0.36 | 2.16 | 1.28 | 0.26 | 2.12 | 0.98 | 0.28 | 0.50 | 0.35 | 0.61 | 0.54 |
| | | Ba | La | Fa | Bb | Lb | Fb | Bc | Lc | Fc | Brwr | Lrwr | Brwc | Lrwc |
| 216 | LIN | 2.91 | 4.54 | 5.19 | 5.13 | 7.16 | 9.02 | 2.94 | 4.10 | 5.30 | 4.98 | 5.57 | 5.46 | 5.77 |
| 216 | EPA | 1.73 | 1.19 | 0.92 | 2.01 | 1.45 | 1.13 | 1.16 | 0.93 | 0.86 | 0.78 | 0.79 | 0.89 | 0.76 |
| 216 | DHA | 1.84 | 1.45 | 0.92 | 2.14 | 1.42 | 0.82 | 2.74 | 1.57 | 0.48 | 0.51 | 0.47 | 0.75 | 0.58 |

TABLE 4

"MARKET EGG" n-3 PUFA PROFILE

[EXPRESSED AS PERCENT OF CRUDE LIPID]

| | |
|---|---|
| Linolenic Acid | 0.16 |

TABLE 4-continued

"MARKET EGG" n-3 PUFA PROFILE
[EXPRESSED AS PERCENT OF CRUDE LIPID]

| | |
|---|---|
| Eicosapentaenoic Acid | 0.04 |
| Docosahexaenoic Acid | 0.58 |

TABLE 5

"OMEGA EGG" n-3 PUFA PROFILE
[EXPRESSED AS PERCENT OF CRUDE LIPID]

| | Weeks of Experimental Diet | | | | | | | | | |
|---|---|---|---|---|---|---|---|---|---|---|
| | #1 | #2 | #3 | #4 | #5 | #6 | #7 | #8 | #9 | #10 |
| Linolenic Acid | 0.20 | 0.42 | 0.44 | 0.42 | 0.41 | 0.31 | 0.30 | 0.36 | 0.46 | 0.42 |
| Eicosapentaenoic Acid | 0.11 | 0.64 | 0.82 | 0.74 | 0.84 | 0.39 | 0.64 | 0.59 | 0.63 | 0.53 |
| Docosahexaenoic Acid | 0.88 | 3.12 | 3.20 | 3.14 | 3.62 | 2.64 | 2.82 | 2.57 | 2.89 | 2.67 |

References

1. Ehrstrom, M. CH, Acta Medica Scandinavica, 140(6), 416–422, 1951.
2. Bangana, H. O., and Dyerberg, J., Acta Medica Scandinavica 210, 245–248, 1981.
3. Dyerberg, J. and Bang, H. O., Scand, J. CLIN. LAB. INVEST. 42, SUPPL. 161, 7–13, 1987.
4. Kagawa et al., J. Nutr. Sci. Uitaminol. 28, 441–453, 1982.
5. Kromhout et al., The New England Journal of Meicine, 312(19), 1205–1209, May 9, 1985.
6. Dyerberg, J., Observations on Populations In Greenland and Denmark, Gronland 1978, Minestry of Greenland. 1979.
7. Saymor, R., and Verel, D., The Lancet, 1335, June 11, 1983.
8. Sanders, T. A. B., Clinical Science 65, 343–350, 1983.
9. Hay et al., The Lancet, 1269–1772, June 5, 1982.
10. Woodcock B. E., British Medical Journal 288, 592–594, 1984.
11. Phillipson et al., The New England Journal of Medicine 312, No. 19, 1210–1216, May 9, 1985.
12. Kinsell et al., Diabetes 10, No. 4, 316–318, 1961.
13. Sanders, T. A. B. and Hochland, M. C., British Journal of Nuitrition 50, 521–529, 1983.
14. Sanders, T. A. B. and Roshanai, F., Clinical Science 64, 91–99, 1983.
15. Saymor, R. and Verel, D., IRCS Medical Science: Biochemistry, Cardiovascular Systems; Clinical Biochemistry; Clinical Pharmacology and Therapeutics; Hematology; Metabolism and Nutrition 8, 378–379, 1980.
16. Sanders et al., Clinical Science 61, 317–324, 1981.
17. Saymor, R. and Verel, D., The Lancet, 272, July 31, 1982.
18. Jorgensen, K. A., Nielsen, A. H. and Dyerberg J., Acta Med Scand 219, 473–479, 1986.
19. Mortensen et al., Thromb Haemostas (Stuttgart) 50(2), 543–546, 1983.
20. Kobayashi S., The Lancet, 197, July 25, 1981.
21. Dyerber J., Phil. Trans. R. Soc. Lond. B294, 373–381 (1981).
22. Knapp et al, Abstracts Circulation FL, Supp III, 198, Oct. 1985.
23. Knapp, H. R., The New England Journal of Medicine 314 (15), 937–942, Apr. 10, 1986.
24. Saynor, R., Vereland, D. and Gillot, T., Atherosclerosis 50, 3–10, 1984.
25. Saynor R., Verel D. and Gillot T., Thromb. Haemostas. Abstract, 1981.
26. Sanders, T. A. B., and Younger, K. M., Br. J. Nutr 45, 613–616, 1987.
27. Lee et al., The New England Journal of Medicine 312(19), 1217–1224, May 9, 1985.
28. Prickett, J. D., J. Clin. Invest 68, 556–559, 1981.
29. Prickett, J. D., Arthritis and Rheumatism 26(2), 133–139, Feb. 1983.
30. Kelley et al., The Journal of Immunology 134(3), 1914–1919, Mar. 1985.
31. Corman, L. C., Seminars in Arthritis and Rheumatism 15 (1), 61–69, Aug. 1985.
32. Berry, E. M. and Hirsch, J., The American Journal of Clinical Nutrition 44, 336–340, Sept. 1986.
33. Johnston, P. U., Advances in Lipid Research 21, 103–141, 1985.
34. Hepburn, F. N., Exler, J., and Weihrauch, J. L., Journal of the American Dietetic Association 86(6), 788–793, June 1986.
35. Bang, H. O., Dyerberg, J., and Hjorne, N., Acta Med Scand 200, 69–73, 1976.
36. Bang, H. O., Dyerberg, J., and Sinclair, H. M., The American Journal of Clinical Nutrition 33, 2657–2661, 1980.
37. Puustinen, T., Punnonen, K., and Uotila, P., Acta Med Scand 218, 59–62, 1985.
38. Simopoulos, A. P., and Salem, N., New England J. Med 315(13), 833, 1986.
39. Vogl, T. P., NIH Guide For Grants and Contracts 14 (13), 35–39, Dec. 6, 1985.
40. Ackman, R. G., National Acadamy of Sciences, ISBN 0-309-02520-6, 1976.
41. Ackman, R. G., Corp. Biochem. Physiol., 22, 907–922, 1967.
42. Ackman, R. G., Lipids 9(12), 1032–1035, 1974.

What is claimed is:

1. A method of increasing the concentration of omega-3, polyunsaturated fatty acids in poultry which comprises administering to the poultry a poultry feed consisting essentially of a mixture of a conventional poultry feed and an amount of preformed omega-3, polyunsaturated fatty acid or a metabolic precursor thereof effective to increase the concentration of omega-3, polyunsaturated fatty acids in poultry which eat the feed, the metabolic precursor thereof being selected from the group consisting of linolenic acid, fish, menhaden oil, algae, and omega-3, polyunsaturated fatty acids having a carbon chain of less than about 18 carbons, so as to increase the concentration of omega-3, polyunsaturated fatty acids in the poultry.

2. A method of claim 1, wherein the poultry feed consists essentially of the metabolic precursor linolenic acid in the form of linseed oil.

3. A method of claim 1, wherein the poultry feed consists essentially of the metabolic precursor menhaden oil.

4. A method of increasing the concentration of omega-3, polyunsaturated fatty acids in poultry eggs which comprises administering to the poultry egg layers a poultry feed consisting essentially of a mixture of a conventional poultry feed and an amount of preformed omega-3, polyunsaturated fatty acid or a metabolic precursor thereof effective to increase the concentration of omega-3, polyunsaturated fatty acids in poultry which eat the feed, the metabolic precursor thereof being selected from the group consisting of linolenic acid, fish menhaden oil, algae, and omega-3, polyunsaturated fatty acids having a carbon chain of less than about 18 carbons, so as to increase the concentration of omega-3, polyunsaturated fatty acids in the eggs.

5. A method of claim 4, wherein the poultry feed consists essentially of the metabolic precursor linolenic acid in the form of linseed oil.

6. A method of claim 4, wherein the poultry feed consists essentially of the metabolic precursor menhaden oil.

7. A method of claim 6, wherein menhaden oil comprises at least 5% by weight of the poultry egg layers' diet.

* * * * * ial

(12) EX PARTE REEXAMINATION CERTIFICATE (6120th)
United States Patent
Weiss et al.

(10) Number: US 4,918,104 C1
(45) Certificate Issued: Feb. 19, 2008

(54) METHOD AND COMPOSITION FOR INCREASING THE CONCENTRATION OF OMEGA-3 POLYUNSATURATED FATTY ACIDS IN POULTRY AND POULTRY EGGS AND POULTRY AND EGGS RESULTING THEREFROM

(76) Inventors: Howard S. Weiss, 45 Hillpark Ave., Great Neck, NY (US) 11021; Carl S. Schwartz, R.D. 2192 Kirby La., Muttontown, NY (US) 11791

Reexamination Request:
No. 90/002,154, Oct. 2, 1990

Reexamination Certificate for:
Patent No.: 4,918,104
Issued: Apr. 17, 1990
Appl. No.: 07/062,890
Filed: Jun. 16, 1987

(51) Int. Cl.
*A23K 1/18* (2006.01)
*A23K 1/16* (2006.01)
*A61K 31/20* (2006.01)
*A61K 31/185* (2006.01)

(52) U.S. Cl. .......................................... 514/560; 426/2
(58) Field of Classification Search ................. 514/560; 424/2
See application file for complete search history.

(56) References Cited

U.S. PATENT DOCUMENTS 2,879,162 A   3/1959   Baldini et al. .............. 514/560

FOREIGN PATENT DOCUMENTS

JP            216658    9/1986    ................. 514/560

OTHER PUBLICATIONS

Sanders, T.A.B et al., Clinical Science, 1981, pp. 16–23.*
Sanders, T.A.B. et al., Clinical Science, 1983, pp. 91–99.*
Davidson, Michael H. et al., Cardiovascular Reviews & Reports, vol. 7, No. 5, May 1986, pp. 461–471.*
Cruickshank, E.M. 1934. CXXXVI. Biochem. J. 28:967–997.*
Edwards, H.M. & May, K.N. 1965. Poultry Sci. 44:685–689.*
Edwards, H.M., Denman, F. Abou–Ashour, A. & Nugava, D. 1973. Poultry Sci. 52: 934–948.*
Couch, J.R. & Saloma, A.E. 1973. Effect of diet on triglyceride structure and compositon of egg yolk lipids. Lipids vol. 8, No. 7:385–392.
Cruickshank, E.M. 1934. CXXXVI. Studies in the fat metabolism in the fowl. I. The composition of egg fat and depot fat of the fowl as affected by ingestion of large amounts of different fats. Biochem. J. 28:967–997.
Edwards, H.M. & May, K.N. 1965. Studies with menhaden oil in practical–type broiler rations. Poultry Sci. 44:685–689.

Edwards, H.M., Denman, F., Abou–Ashour, A. & Nugara, D. 1973, 1. Influences of age, sex and type of dietary fat supplementation on total carcass and fatty acid composition. Poultry Sci. 52:934–948.
Fisher, H. & Leveille, G.A. 1957. Observations on the cholesterol, linoleic and linolenic acid content of eggs as influenced by dietary fats. J. Nutrition 63:119–129.
Hulan, H.W. & Proudfoot, F.G. 1981. Replacement of soybean meal in chicken broiler diets by rapeseed meal and fish meal complementary sources of dietary protein. Can. J. Animal Sci. 61:999–1004.
Hulan, H.W., Proudfoot, F.G. & Nash, D.M. 1984. The effects of different dietary fat sources on general performance and carass fatty acid compositoin of broiler chickens. Poultry Sci. 63:324–332.
Lipstein, B. & Hurwitz, S. 1980. The Nutritional Value of Algae for Poultry. Dried Chlorella in Broiler Diets. British Poultry Science 21:9–21.
Lipstein, B. & Hurwitz, S. 1980a. The Nutrtional and Economic Value of Algae for Poultry. Algae Biomass, Schelef, G. and Soeder, C.J., eds., North–Holland Biomedical Press, pp. 667–685.
Lipstein, B., Hurwitz, S. & Bernstein, S. 1980. The Nutritional Value of Algae for Poultry. Dried Chlorella in Layer Diets. British Poultry Science 21:23–27.
Marion, J.E. & Woodruff, J.G. 1963. The fatty acid composition of breast, thigh, and skin tissues of chicken broilers as influenced by dietary fats. Poultry Sci. 42:1202–1207.
Mcleod, J.A. 1981. Nutritional factors influencing carcass fat in broilers—A review. Worlds Poultry Sci. J. 37:194–200.
Miller, D. & Robisch, P. 1969. Comparative effects of herring, menhaden and safflower oils on broiler tissues fatty acid composition and flavor. Poultry Sci. 48:2146–2157.
Miller, D., Leong, K.C. & Smith, P. 1969. Effect of feeding and withdrawal of menhaden oil on the w3 and w6 fatty acid content of broiler tissues. J. Food Sci. 34:136–141.

(Continued)

*Primary Examiner*—Michael G. Hartley

(57) ABSTRACT

This invention provides a method of increasing the concentration of omega-3, polyunsaturated fatty acids in poultry which comprises administering to the poultry an effective amount of preformed omega-3, polyunsaturated fatty acid or a metabolic precursor thereof.

The invention also involves a poultry feed composition useful in effecting this result.

Also disclosed is a method of increasing the concentration of omega-3, polyunsaturated fatty acids in poultry eggs which comprises administering to the poultry egg layers an effective amount of preformed omega-3, polyunsaturated fatty acid or a metabolic precursor thereof.

Further disclosed is a chicken and a poultry egg, each having omega-3, polyunsaturated fatty acids at a concentration greater than that which naturally occurs or is normally present.

OTHER PUBLICATIONS

Miller, D., Gruger, E.H., Leong, K.C. & Knobl, G.M. 1967. Dietary effect of menhaden–oil ethyl esters on the fatty acid pattern of broiler muscle lipids. Poult. Sci. 46:438–444.

Murty, N.L. & Reiser, R. 1961. Influence of graded levels of dietary linoleic and linolenic acids on the fatty acid composition of hens' eggs. J. Nutrition 75:287–294.

Navarro, J.G., Saavedra, J.C., Borie, F.B. & Caiozzi, M.M. 1972. Influence of dietary fish meal on egg fatty acid composition. J. Sci. Food. Agric. 23:1287–1292.

Opstvedt, J. 1973. Influence of residual lipids on the nutritive value of fish meal. V. Digestion and deposition of marine fatty acids in chickens. Acta Agric. Scand. 23:217–224.

Reiser, R. 1951. The syntheses and interconversions of polyunsatured fatty acids by the laying hen. J. Nutrition 106:443–450.

CRC Handbook of Microalgal Mass Culture, Richard, Amos, ed., CRC Press, Inc., Boca Raton, Florida, pp. 334–398 (1986).

Derwent Abstract of J6 0169–418A Feb. 15, 1984.

Derwent Abstract of J5 7086–254 Nov. 18, 1980.

Derwent Abstract of J6 2163–669A.

Derwent Abstract of J6 0132–916A.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–7 are cancelled.

* * * * *